United States Patent
Lau et al.

(10) Patent No.: US 11,661,597 B2
(45) Date of Patent: May 30, 2023

(54) ROBUST QUANTIFICATION OF SINGLE MOLECULES IN NEXT-GENERATION SEQUENCING USING NON-RANDOM COMBINATORIAL OLIGONUCLEOTIDE BARCODES

(71) Applicant: The Board of Trustees of the Leland Stanford Junior University, Stanford, CA (US)

(72) Inventors: Billy Tsz Cheong Lau, Palo Alto, CA (US); Hanlee P. Ji, Stanford, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 564 days.

(21) Appl. No.: 15/560,136

(22) PCT Filed: Apr. 13, 2016

(86) PCT No.: PCT/US2016/027356
§ 371 (c)(1),
(2) Date: Sep. 20, 2017

(87) PCT Pub. No.: WO2016/168351
PCT Pub. Date: Oct. 20, 2016

(65) Prior Publication Data
US 2018/0100145 A1    Apr. 12, 2018

Related U.S. Application Data

(60) Provisional application No. 62/148,047, filed on Apr. 15, 2015.

(51) Int. Cl.
*C12N 15/10* (2006.01)
*C12Q 1/6855* (2018.01)
*C12Q 1/6806* (2018.01)

(52) U.S. Cl.
CPC ..... *C12N 15/1065* (2013.01); *C12N 15/1093* (2013.01); *C12Q 1/6806* (2013.01); *C12Q 1/6855* (2013.01); *C12Q 2525/191* (2013.01); *C12Q 2535/122* (2013.01); *C12Q 2563/179* (2013.01); *C12Q 2565/514* (2013.01)

(58) Field of Classification Search
CPC ..................................................... C12N 15/10
See application file for complete search history.

(56) References Cited

U.S. PATENT DOCUMENTS

| | | | |
|---|---|---|---|
| 2013/0023423 A1 | 1/2013 | Kavanagh et al. | |
| 2013/0231253 A1* | 9/2013 | Amorese | C12N 15/1068 506/2 |
| 2014/0066317 A1* | 3/2014 | Talasaz | C12Q 1/6869 506/2 |
| 2014/0228255 A1* | 8/2014 | Hindson | C12Q 1/6874 506/26 |
| 2017/0233727 A1* | 8/2017 | Zhou | C12N 15/1093 506/4 |

FOREIGN PATENT DOCUMENTS

| | | |
|---|---|---|
| WO | WO 2004/016811 | 2/2004 |
| WO | WO 2009/133466 | 11/2009 |
| WO | WO 2014/071361 | 5/2014 |
| WO | WO 2015/044412 | 4/2015 |

OTHER PUBLICATIONS

Arneson et al., Whole-Genome Amplification by Improved Primer Extension Preamplification PCR (I-PEP-PCR), CSH Protocols, 2008, 3(1), 1-5—(Year: 2008).*
Adey et al., "Rapid, low-input, low-bias construction of shotgun fragment libraries by high-density in vitro transposition", Genome Biology, 2010, 11:R119.
Bystrykh, "Generalized DNA Barcode Design Based on Hamming Codes", PLoS ONE, 2012, 7(5):e36852.

* cited by examiner

*Primary Examiner* — Amy M Bunker
(74) *Attorney, Agent, or Firm* — James S. Keddie; Bozicevic, Field & Francis LLP

(57) ABSTRACT

A population of nucleic acid adaptors is provided. In some embodiments, the population contains at least 50,000 different molecular barcode sequences, where the barcode sequences are double-stranded and at least 90% of the barcode sequences have an edit distance of at least 2. In certain cases, the adaptor may have an end in which the top and bottom strands are not complementary (i.e., may be in the form of a Y-adaptor). In some embodiments and depending on the how the adaptor is going to be employed, the other end of the adaptor may have a ligatable end or may be a transposon end sequence.

9 Claims, 14 Drawing Sheets

ROBUST QUANTIFICATION OF SINGLE MOLECULES IN NEXT-GENERATION SEQUENCING USING NON-RANDOM COMBINATORIAL OLIGONUCLEOTIDE BARCODES

CROSS-REFERENCE TO RELATED APPLICATIONS

This application is a § 371 national phase of International Application No. PCT/US2016/027356, filed on Apr. 13, 2016, which claims the benefit of U.S. Application Ser. No. 62/148,047, filed on Apr. 15, 2015, which applications are incorporated by reference herein.

GOVERNMENT RIGHTS

This invention was made with Government support under contract HG000205 awarded by the National Institutes of Health. The Government has certain rights in the invention.

BACKGROUND

Somatic variation is the fundamental driver of cancer and its accurate interpretation in cancer genomes is fundamental to understanding its development and guiding therapy. The investigation of cancer genomes at the DNA and RNA level thus enables the discovery of variants that may inform treatment. Typically, the characterization of genetic information in biological samples requires both accurate quantification and characterization of variants. For example, applications such as somatic variant and transcriptome analysis require high depth sequencing, usually in the order of hundred- or thousand-fold coverage, in order to confirm variants. However, short-read sequencing platforms suffer from a fundamental and often overlooked trade-off between quantitation and detection: at high coverages required to confirm genetic or isoform variants, it becomes difficult to distinguish PCR duplicates from unique molecules that have coincidentally overlapping mapping locations. This results in a persistent 'noise' whereby the quantification of sequencing data becomes confounded. In particular, transcriptomes are approximately 1000-fold smaller than the human genome but are sequenced at over 10 million reads per sample, meaning that extensive correction to account for duplicate molecules is required.

Experimental methods have also been developed to label DNA fragments with nucleotide barcodes that can be bioinformatically extracted (see, e.g., Casbon (Nucl. Acids Res. 2011 39: e81), Fu (Proc. Natl. Acad. Sci. 2011 108: 9026-9031) and Kivioia (Nat. Methods 2011 9: 72-74)). These barcodes can be rationally designed but scale poorly to samples that require quantification over a large dynamic range. In contrast, barcodes consisting of random nucleotides are able to efficiently label every molecule in a DNA library; their ease of use has resulted in several works investigating single cell gene expression. However, a randomly generated barcode carries no information about errors that may occur during the entire sequencing workflow. These downstream errors, which are accumulated in the entire read during PCR or the sequencing itself, propagate barcode errors that are difficult to bioinformatically detect.

Described herein is a strategy for tagging a sample with billions to over trillions of unique error-correctible barcode tags without prior knowledge of the DNA insert context. The production of the barcode tags is based on the combinatorial assembly of a small set of rationally designed error-resistant oligonucleotides that allow for an exponential expansion in the total number of possible barcodes comparable to methods utilizing random nucleotides.

SUMMARY

A population of nucleic acid adaptors is provided. In some embodiments, the population contains at least 50,000 different molecular barcode sequences, wherein the barcode sequences are double-stranded and at least 90% of the barcode sequences have an edit distance of at least 2. In certain cases, the adaptor may have an end in which the top and bottom strands are not complementary (i.e., may be in the form of a Y-adaptor). In some embodiments and depending on the how the adaptor is going to be employed, the other end of the adaptor may have a ligatable end or may be a transposon end sequence.

The population of adaptors may be used in a variety of different methods. For example, the adaptors may be ligated onto DNA fragments or transferred onto DNA fragments using a transposase, thereby resulting in a population of fragments that are tagged by barcodes that can still be read even if the sequence reads for the barcode contains an error. In other embodiments, the bottom strand of the adaptor may be removed, leaving a top strand that can be used to tag other sequences, e.g., RNA, cDNA, or genomic DNA by primer extension, thereby resulting in a population of tagged primer extension products that contain barcodes that can still be read even if the sequence reads for the barcode contains an error.

After tagging, the tagged sequence may be amplified using primers that lie outside of the added tags to produce amplified molecules that contain at least a single barcode at one end and sometimes a barcode at both ends. The amplified molecules can be sequenced and the number of different molecules corresponding to a particular sequence of interest can be determined by counting the number of different tag sequences that are associated with the particular sequence of interest. If paired-end sequencing is used, over a billion molecules can be discriminated using the tags.

The barcodes can be used, for example, to identify sequence errors, for allele calling, for assigning confidence, to perform copy number analysis and to estimate gene expression levels.

Methods for making the population of adaptors described above are also provided.

BRIEF DESCRIPTION OF THE FIGURES

Certain aspects of the following detailed description are best understood when read in conjunction with the accompanying drawings. It is emphasized that, according to common practice, the various features of the drawings are not to scale. On the contrary, the dimensions of the various features are arbitrarily expanded or reduced for clarity. Included in the drawings are the following figures.

DEFINITIONS

Figure 1A:
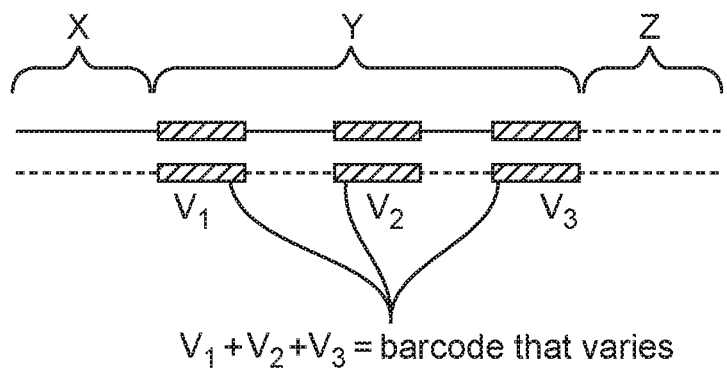
FIGS. 1A and 1B schematically illustrate some of the features of the present population of adaptors.

Before describing exemplary embodiments in greater detail, the following definitions are set forth to illustrate and define the meaning and scope of the terms used in the description.

Numeric ranges are inclusive of the numbers defining the range. Unless otherwise indicated, nucleic acids are written left to right in 5' to 3' orientation; amino acid sequences are written left to right in amino to carboxy orientation, respectively.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

The term "sample" as used herein relates to a material or mixture of materials, typically, although not necessarily, in liquid form, containing one or more analytes of interest. The nucleic acid samples used herein may be complex in that they contain multiple different molecules that contain sequences. Genomic DNA and cDNA made from mRNA from a mammal (e.g., mouse or human) are types of complex samples. Complex samples may have more then $10^4$, $10^5$, $10^6$ or $10^7$ different nucleic acid molecules. A DNA target may originate from any source such as genomic DNA, cDNA (from RNA) or artificial DNA constructs. Any sample containing nucleic acid, e.g., genomic DNA made from tissue culture cells, a sample of tissue, or an FFPE samples, may be employed herein.

The term "nucleic acid sample," as used herein denotes a sample containing nucleic acids. A nucleic acid samples used herein may be complex in that they contain multiple different molecules that contain sequences. Genomic DNA, RNA (and cDNA made from the same) from a mammal (e.g., mouse or human) are types of complex samples. Complex samples may have more then $10^4$, $10^5$, $10^6$ or $10^7$ different nucleic acid molecules. A target molecule may originate from any source such as genomic DNA, or an artificial DNA construct. Any sample containing nucleic acid, e.g., genomic DNA made from tissue culture cells or a sample of tissue, may be employed herein.

The term "mixture", as used herein, refers to a combination of elements, that are interspersed and not in any particular order. A mixture is heterogeneous and not spatially separable into its different constituents. Examples of mixtures of elements include a number of different elements that are dissolved in the same aqueous solution and a number of different elements attached to a solid support at random positions (i.e., in no particular order). A mixture is not addressable. To illustrate by example, an array of spatially separated surface-bound polynucleotides, as is commonly known in the art, is not a mixture of surface-bound polynucleotides because the species of surface-bound polynucleotides are spatially distinct and the array is addressable.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., peptide nucleic acid or PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, thymine, uracil (G, C, A, T and U respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylenecarbonyl bonds. A locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid", or "UNA", is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is incorporated by reference herein for disclosure of UNA.

The term "oligonucleotide" as used herein denotes a single-stranded multimer of nucleotides of from about 2 to 200 nucleotides, or up to 500 nucleotides in length. Oligonucleotides may be synthetic or may be made enzymatically, and, in some embodiments, are 30 to 150 nucleotides in length. Oligonucleotides may contain ribonucleotide monomers (i.e., may be oligoribonucleotides) or deoxyribonucleotide monomers, or both ribonucleotide monomers and deoxyribonucleotide monomers. An oligonucleotide may be 10 to 20, 11 to 30, 31 to 40, 41 to 50, 51 to 60, 61 to 70, 71 to 80, 80 to 100, 100 to 150 or 150 to 200 nucleotides in length, for example.

"Primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Usually primers are extended by a DNA polymerase. Primers are generally of a length compatible with their use in synthesis of primer extension products, and are usually are in the range of between 8 to 100 nucleotides in length, such as 10 to 75, 15 to 60, 15 to 40, 18 to 30, 20 to 40, 21 to 50, 22 to 45, 25 to 40, and so on, more typically in the range of between 18 to 40, 20 to 35, 21 to 30 nucleotides long, and any length between the stated ranges. Typical primers can be in the range of between 10 to 50 nucleotides long, such as 15 to 45, 18 to 40, 20 to 30, 21 to 25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

The term "hybridization" or "hybridizes" refers to a process in which a nucleic acid strand anneals to and forms a stable duplex, either a homoduplex or a heteroduplex, under normal hybridization conditions with a second complementary nucleic acid strand, and does not form a stable duplex with unrelated nucleic acid molecules under the same normal hybridization conditions. The formation of a duplex is accomplished by annealing two complementary nucleic acid strands in a hybridization reaction. The hybridization reaction can be made to be highly specific by adjustment of the hybridization conditions (often referred to as hybridization stringency) under which the hybridization reaction takes place, such that hybridization between two nucleic acid strands will not form a stable duplex, e.g., a duplex that retains a region of double-strandedness under normal stringency conditions, unless the two nucleic acid strands contain a certain number of nucleotides in specific sequences which are substantially or completely complementary. "Normal hybridization or normal stringency conditions" are readily determined for any given hybridization reaction. See, for example, Ausubel et al., Current Protocols in Molecular Biology, John Wiley & Sons, Inc., New York, or Sambrook et al., Molecular Cloning: A Laboratory Manual, Cold Spring Harbor Laboratory Press. As used herein, the term "hybridizing" or "hybridization" refers to any process by which a strand of nucleic acid binds with a complementary strand through base pairing.

A nucleic acid is considered to be "selectively hybridizable" to a reference nucleic acid sequence if the two sequences specifically hybridize to one another under moderate to high stringency hybridization and wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions include hybridization at about 42C in 50% formamide, 5×SSC, 5×Denhardt's solution, 0.5% SDS and 100 ug/ml denatured carrier DNA followed by washing two times in 2×SSC and 0.5% SDS at room temperature and two additional times in 0.1×SSC and 0.5% SDS at 42° C.

The term "duplex," or "duplexed," as used herein, describes two complementary polynucleotides that are base-paired, i.e., hybridized together.

The term "amplifying" as used herein refers to the process of synthesizing nucleic acid molecules that are complementary to one or both strands of a template nucleic acid. Amplifying a nucleic acid molecule may include denaturing the template nucleic acid, annealing primers to the template nucleic acid at a temperature that is below the melting temperatures of the primers, and enzymatically elongating from the primers to generate an amplification product. The denaturing, annealing and elongating steps each can be performed one or more times. In certain cases, the denaturing, annealing and elongating steps are performed multiple times such that the amount of amplification product is increasing, often times exponentially, although exponential amplification is not required by the present methods. Amplification typically requires the presence of deoxyribonucleoside triphosphates, a DNA polymerase enzyme and an appropriate buffer and/or co-factors for optimal activity of the polymerase enzyme. The term "amplification product" refers to the nucleic acid sequences, which are produced from the amplifying process as defined herein.

The terms "determining", "measuring", "evaluating", "assessing," "assaying," and "analyzing" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

The term "genomic region", as used herein, refers to a region of a genome, e.g., an animal or plant genome such as the genome of a human, monkey, rat, fish or insect or plant.

The term "terminal nucleotide", as used herein, refers to the nucleotide at either the 5' or the 3' end of a nucleic acid strand. The nucleic acid strand may be in double-stranded (i.e., duplexed) or in single-stranded form.

The term "ligating", as used herein, refers to the enzymatically catalyzed joining of the terminal nucleotide at the 5' end of a first DNA molecule to the terminal nucleotide at the 3' end of a second DNA molecule.

A "plurality" contains at least 2 members. In certain cases, a plurality may have at least 2, at least 5, at least 10, at least 100, at least 100, at least 10,000, at least 100,000, at least $10^6$, at least $10^7$, at least $10^8$ or at least $10^9$ or more members.

If two nucleic acids are "complementary", they hybridize with one another under high stringency conditions. The term "perfectly complementary" is used to describe a duplex in which each base of one of the nucleic acids base pairs with a complementary nucleotide in the other nucleic acid. In many cases, two sequences that are complementary have at least 10, e.g., at least 12 or 15 nucleotides of complementarity.

The term "strand" as used herein refers to a nucleic acid made up of nucleotides covalently linked together by covalent bonds, e.g., phosphodiester bonds. In a cell, DNA usually exists in a double-stranded form, and as such, has two complementary strands of nucleic acid referred to herein as the "top" and "bottom" strands. In certain cases, complementary strands of a chromosomal region may be referred to as "plus" and "minus" strands, the "first" and "second" strands, the "coding" and "noncoding" strands, the "Watson" and "Crick" strands or the "sense" and "antisense" strands. The assignment of a strand as being a top or bottom strand is arbitrary and does not imply any particular orientation, function or structure. The nucleotide sequences of the first strand of several exemplary mammalian chromosomal regions (e.g., BACs, assemblies, chromosomes, etc.) is known, and may be found in NCBI's Genbank database, for example.

The term "top strand," as used herein, refers to either strand of a nucleic acid but not both strands of a nucleic acid. When an oligonucleotide or a primer binds or anneals "only to a top strand," it binds to only one strand but not the other. The term "bottom strand," as used herein, refers to the strand that at least partly complementary to the "top strand." When an oligonucleotide binds or anneals "only to one strand," it binds to only one strand, e.g., the first or second strand, but not the other strand. In certain cases and as will be described in greater detail below, two strands may be annealed to one another in a duplex but there may be part of the duplex that is not annealed (e.g., because the sequences are not complementary). In these cases, the strands that are not annealed may still be referred to as being "top" and "bottom" strands because they are covalently linked to strands that are annealed to one another.

The term "covalently linking" refers to the production of a covalent linkage between two separate molecules, e.g., the top and bottom strands of a double stranded nucleic acid. Ligating is a type of covalent linking.

The term "denaturing," as used herein, refers to the separation of at least a portion of the base pairs of a nucleic acid duplex by placing the duplex in suitable denaturing conditions. Denaturing conditions are well known in the art. In one embodiment, in order to denature a nucleic acid duplex, the duplex may be exposed to a temperature that is above the Tm of the duplex, thereby releasing one strand of the duplex from the other. In certain embodiments, a nucleic acid may be denatured by exposing it to a temperature of at least 90° C. for a suitable amount of time (e.g., at least 30 seconds, up to 30 mins). In certain embodiments, fully denaturing conditions may be used to completely separate the base pairs of the duplex. In other embodiments, partially denaturing conditions (e.g., with a lower temperature than fully denaturing conditions) may be used to separate the base pairs of certain parts of the duplex (e.g., regions enriched for A-T base pairs may separate while regions enriched for G-C base pairs may remain paired.) Nucleic acid may also be denatured chemically (e.g., using urea or NaOH).

The term "sequencing", as used herein, refers to a method by which the identity of at least 10 consecutive nucleotides (e.g., the identity of at least 20, at least 50, at least 100 or at least 200 or more consecutive nucleotides) of a polynucleotide are obtained.

The term "next-generation sequencing" refers to the so-called parallelized sequencing-by-synthesis or sequencing-by-ligation platforms currently employed by Illumina, Life Technologies, and Roche etc. Next-generation sequencing methods may also include nanopore sequencing methods or electronic-detection based methods such as Ion Torrent technology commercialized by Life Technologies.

The term "extending", as used herein, refers to the extension of a primer by the addition of nucleotides using a polymerase. If a primer that is annealed to a nucleic acid is extended, the nucleic acid acts as a template for extension reaction.

The term "barcode sequence" or "molecular barcode", as used herein, refers to a unique sequence of nucleotides used to a) identify and/or track the source of a polynucleotide in a reaction and/or b) count how many times an initial molecule is sequenced (e.g., in cases where substantially every molecule in a sample is tagged with a different sequence, and then the sample is amplified). A barcode sequence may be at the 5'-end, the 3'-end or in the middle of an oligonucleotide, or both the 5' end and the 3' end. Barcode sequences may vary widely in size and composition; the following references provide guidance for selecting sets of barcode sequences appropriate for particular embodiments: Brenner, U.S. Pat. No. 5,635,400; Brenner et al, Proc. Natl. Acad. Sci., 97: 1665-1670 (2000); Shoemaker et al, Nature Genetics, 14: 450-456 (1996); Morris et al, European patent publication 0799897A1; Wallace, U.S. Pat. No. 5,981,179; and the like. In particular embodiments, a barcode sequence may have a length in range of from 4 to 36 nucleotides, or from 6 to 30 nucleotides, or from 8 to 20 nucleotides.

As used herein, the term "PCR reagents" refers to all reagents that are required for performing a polymerase chain reaction (PCR) on a template. As is known in the art, PCR reagents essentially include a first primer, a second primer, a thermostable polymerase, and nucleotides. Depending on the polymerase used, ions (e.g., $Mg^{2+}$) may also be present. PCR reagents may optionally contain a template from which a target sequence can be amplified.

The term "adjacent to" refers to a distance of less than the longest dimension of a nucleotide. The term "ligatably adjacent to" means that two nucleotides are immediately adjacent to one another on a strand with no intervening nucleotides.

The term "tailed", in the context of a tailed primer or a primer that has a 5' tail, refers to a primer that has a region (e.g., a region of at least 12-50 nucleotides) at its 5' end that does not hybridize to the same target as the 3' end of the primer.

The term "distinguishable sequences" refers to sequences that are different to one another.

The term "target nucleic acid" as use herein, refers to a polynucleotide of interest under study.

The term "target nucleic acid molecule" refers to a single molecule that may or may not be present in a composition with other target nucleic acid molecules. An isolated target nucleic acid molecule refers to a single molecule that is present in a composition that does not contain other target nucleic acid molecules.

The following description explains the formulas used in this disclosure. Certain populations of polynucleotides described herein may be referred being described by a formula (e.g., "X-Y-Z"), meaning that the population, collectively, has a structure defined by the formula and individual molecules of the population have a structure that fall within the scope of the formula. Such formulas follow the established convention in that they describe a polynucleotide having a top strand that is oriented in the 5' to 3' direction. The components of the formula, e.g., "X", "Y", and "Z" refer to separately definable sequences of nucleotides within a polynucleotide, where the sequences are linked together covalently such that a polynucleotide described by a formula is a single molecule. The components of the formula may be immediately adjacent to one another or spaced from one another in the single molecule. In certain cases, other sequence elements, e.g., other primer binding sites, molecular barcodes, promoters, random sequences, etc. may be provided by sequences that are between the components of a formula. Further, each of the various components of a formula may have functions in addition to those described herein. Following convention, the complement of a sequence shown in a formula will be indicated with a prime (') such that the complement of sequence "Y" will be "Y'". Moreover, unless otherwise indicated or implicit from the context, a polynucleotide defined by a formula may have additional sequence at its 3' end, its 5' end or both the 3' and 5' ends.

The term "region" refers to a sequence of nucleotides that can be single-stranded or double-stranded.

The term "amplification sequence" refers to a sequence that, when copied to produce its reverse complement, hybridizes to an amplification primer (e.g., one of a pair of PCR primers), the extension of which will make a complementary copy of the strand that contains amplification sequence. The amplification sequence may be same in all molecules of the population.

The term "variable", in the context of two or more nucleic acid sequences that are variable, refers to two or more nucleic acids that have different sequences of nucleotides relative to one another. In other words, if the polynucleotides of a population have a variable sequence, then the nucleotide sequence of the polynucleotide molecules of the population varies from molecule to molecule. The term "variable" is not to be read to require that every molecule in a population has a different sequence to the other molecules in a population.

The term "edit distance" is minimal number of nucleotide substitutions required to convert one barcode sequence in a population into another barcode of the same population. For example, it takes two nucleotide substitutions to convert barcode A (GATCCCGACCGTA; SEQ ID NO:1) into barcode B (GAACCCGATCGTA; SEQ ID NO:2) and, as such, those barcodes have an edit distance of 2.

The term "at least 90% of the molecular barcode sequences have an edit distance" of at least 2 means that at least 90% of the molecular barcode sequences in the population cannot be converted into another barcode in the population without making at least two amino acid substitutions.

The term "transposon end sequence" refers to a double-stranded sequence to which a transposase (e.g., the Tn5 transposase or variant thereof) binds, where the transposase catalyzes simultaneous fragmentation of a double-stranded DNA sample and tagging of the fragments with sequences that are adjacent to the transposon end sequence (i.e., by "tagmentation"). Methods for tagmenting and transposon end sequences are well known as are (see, e.g., Picelli et al, Genome Res. 2014 24: 2033-40; Adey et al, Genome Biol. 2010 11:R119 and Caruccio et al, Methods Mol. Biol. 2011 733: 241-55, US20100120098 and US20130203605). Kits for performing tagmentation are commercially sold under the tradename NEXTERA™ by Illumina (San Diego, Calif.). The double-stranded form of AGATGTGTATAAGAGACAG (SEQ ID NO:3) is an example of a Tn5 transposon end sequence, although many others are known and are typically 18-20 bp, e.g., 19 bp in length.

The term "adaptor" refers to a nucleic acid that can be joined, either using a ligase or a transposase-mediated reaction, to at least one strands of a double-stranded DNA molecule. In another embodiment, an adaptor may be a Y-adaptor. As would be apparent, one end of an adaptor may contain a transposon end sequence, or may be designed to be compatible with overhangs made by cleavage by a restriction enzyme, or it may have blunt ends or a 5' T overhang. The term "adaptor" refers to molecules that are at least partially double-stranded. An adaptor may be 40 to 150 bases in length, e.g., 50 to 120 bases, although adaptors outside of this range are envisioned.

The term "adaptor-tagged," as used herein, refers to a nucleic acid that has been tagged by an adaptor. The adaptor can be joined to a 5' end and/or a 3' end of a nucleic acid molecule.

The term "tagged DNA" as used herein refers to DNA molecules that have an added adaptor sequence, i.e., a "tag" of synthetic origin. An adaptor sequence can be added (i.e., "appended") by ligation, by a transposase, or by primer extension.

The term "Y-adaptor" refers to an adaptor that contains: a double-stranded region and a single-stranded region in which the opposing sequences are not complementary. The end of the double-stranded region can be joined to target molecules such as double-stranded fragments of genomic DNA, e.g., by ligation or a transposase-catalyzed reaction. Each strand of an adaptor-tagged double-stranded DNA that has been ligated to a Y adaptor is asymmetrically tagged in that it has the sequence of one strand of the Y-adaptor at one end and the other strand of the Y-adaptor at the other end. Amplification of nucleic acid molecules that have been joined to Y-adaptors at both ends results in an asymmetrically tagged nucleic acid, i.e., a nucleic acid that has a 5' end containing one tag sequence and a 3' end that has another tag sequence.

DETAILED DESCRIPTION OF EXEMPLARY EMBODIMENTS

With reference to FIG. 1A, provided herein a population of nucleic acid adaptors of formula X-Y-Z, where region X is an amplification sequence, region Y comprises a molecular barcode having a variable sequence, and region Z comprises a 3' hydroxyl or is a transposon end. As illustrated in FIG. 1A, at least region Y (which contains the molecular barcode) and part of Z may be double stranded. Depending on how the nucleic acid adaptors are made, the barcode in region Y may be one contiguous sequence or may be made up of multiple discontinuous modules. For example, in some cases the molecular barcode may be composed of at least two (e.g., two, three or four or more) modules that are separated by one or more scaffold sequences. As shown, the variable molecular barcode sequence is composed of three discontinuous modules ($V_1$, $V_2$ and $V_3$). As will be described in greater detail below, there are at least 50,000 different molecular barcode sequences (e.g., at least 100,000, at least 200,000, at least 300,000, at least 500,000 or at least 1M different molecular barcode sequences) in the population, and at least 90% of the molecular barcode sequences (e.g., at least 95% or at least at least 98% of the molecular barcode sequences) have an edit distance of at least 2 (e.g., an edit distance of at least 3, at least 4 or at least 5), meaning that the at least 90% of the molecular barcode sequences in the population require a minimum of two nucleotide substitutions in order to become another barcode in the population. Barcode design based on Hamming codes is described in Bystykh (PLoS One. 2012; 7: e36852), which is incorporated by reference herein for those teachings.

Figure 1B:
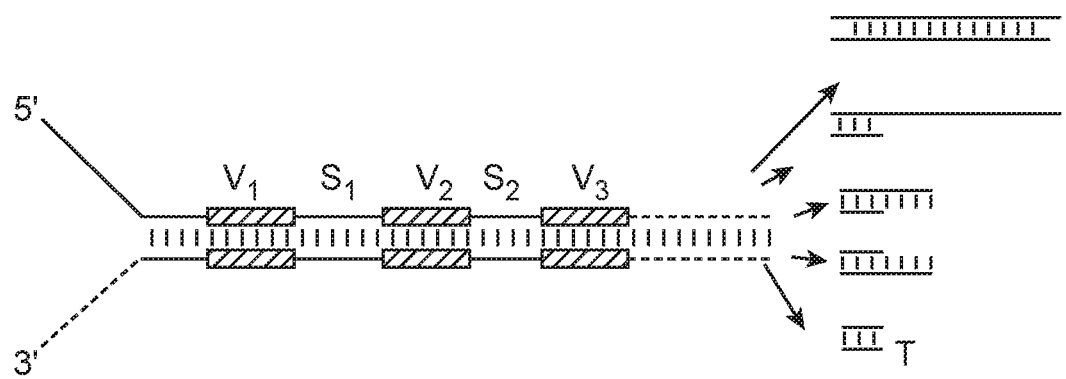

The types of ends that may be present in the adaptors is shown in FIG. 1B. In some embodiments, X may comprises top and bottom strands that are not complementary. In these embodiments, the adaptor will be a "Y" adaptor, as shown. In other embodiments, region X may be double-stranded or single stranded. In all configurations, region X comprises an amplification sequence which, as described above, is a sequence that, when copied to produce its reverse complement, hybridizes to an amplification primer (e.g., one of a pair of PCR primers). Extension of this primer will make a complementary copy of the strand that contains amplification sequence. The amplification sequence may be of any suitable length and composition although it should be sufficiently long to effect specific priming, i.e., it should be at least 12 nucleotides (e.g., at least 13, at least 14, at least 15) in length. Region Z (at the other end of the adaptor) may have any configuration that can be joined to another sequence or extended. For example, as shown, the adaptors may ligatable to double stranded DNA via region Z and, as such, region Z may contain a 5' T overhang, a blunt end, a 3' overhang, or a 5' overhang. In all of these cases, region Z may contain a 5' phosphate in addition to a 3' hydroxyl. In some embodiments (particularly if the bottom strand of the adaptor is going to be removed and the top strand of the adaptor used as a primer), region Z may terminate in a random sequence, oligo-dT, or may be sequence-specific (i.e., specific for a particular target). In other embodiments, region Z is a transposon end sequence, e.g., a Tn5 transposon end sequence. As shown in FIG. 1B, region Y contains a variable molecular barcode sequence composed of three discontinuous modules ($V_1$, $V_2$ and $V_3$), separated by scaffold sequences $S_1$ and $S_2$, which are different and may be in the range of 6 bp to 20 bp or more in length. The barcode itself (after the discontinuous modules have been joined to one another) may have a length of at least 12 nucleotides, e.g., a length of at least 13, at least 14, at least 15, or at least 16 nucleotides. In some embodiments, barcode may be 18 nucleotides in length. The number of nucleotides within each module of the barcode may vary. For example, if the variable barcode is made up of two discontinuous modules, each module may independently contain 5-12 nucleotides, and if the barcode is made up of three discontinuous modules, each module may independently contain 4-10 nucleotides. In some embodiments, if the barcode is made up of three discontinuous modules, each module may independently contain 6 nucleotides.

Figure 2:
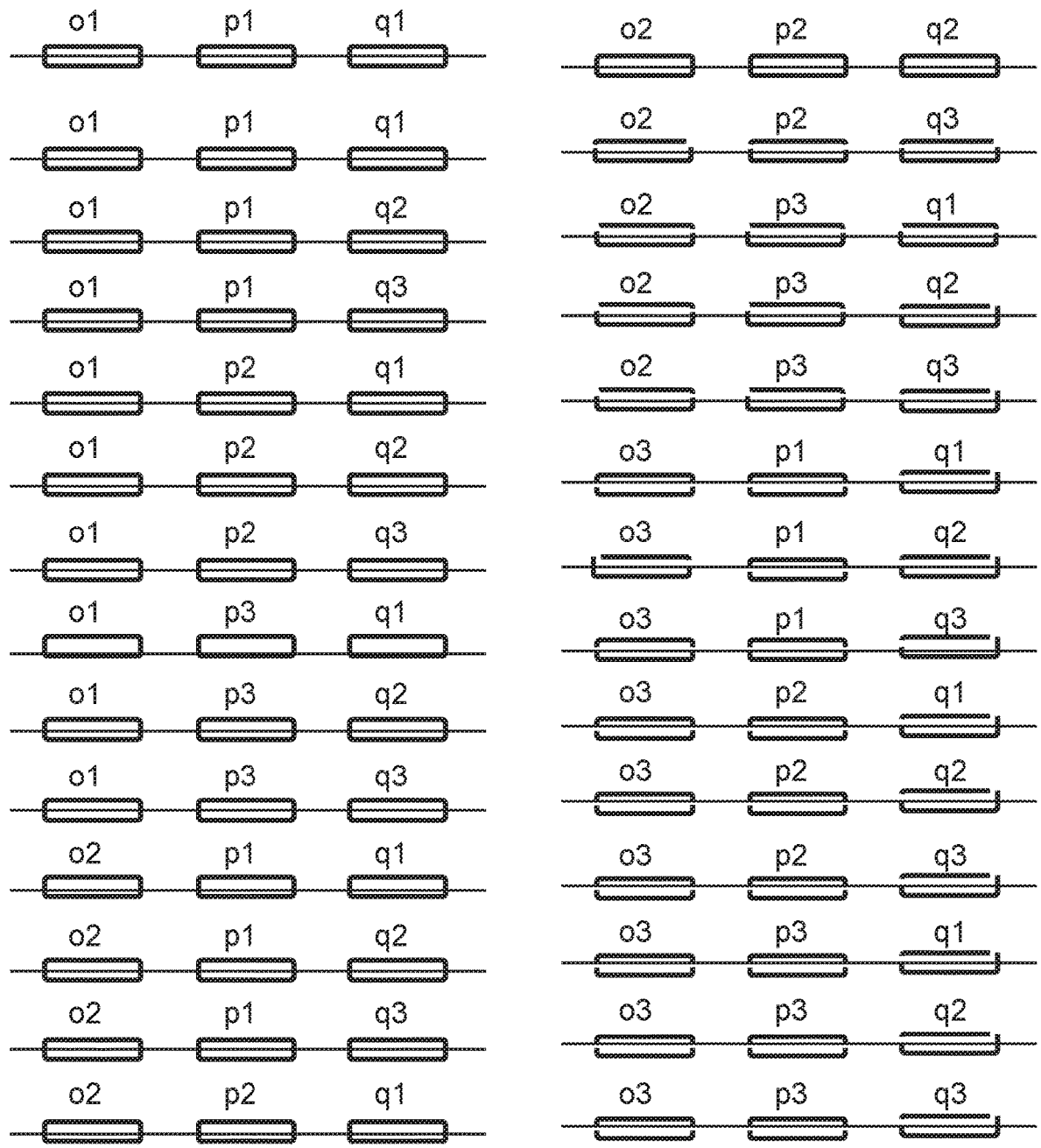
FIG. 2 shows how defined sequences can be combined combinatorially to make a large number of defined barcodes.

FIG. 2 illustrates how a barcode containing three discontinuous modules ("o", "p" and "q"), each containing three nucleotide sequences that are specially designed to provide an error-correcting barcode (o1, o2, o3, p1, p2, p3, q1, q2 and q3) when randomly combined (in a defined order) can produce a much larger number of barcodes of a defined (i.e., not random and error-correctible) sequence. If each discontinuous module is represented by a greater number of sequences (e.g., 10-100 or more), then a much larger number of non-random error correctible barcodes can be produced. For example, if "o", "p" and "q" are each composed of 64 sequences, then the sequences can be combined in the manner shown to produce $64^3$ (i.e., 262,144) error-correctable barcode and, because the sequence are defined and not random, the edit distance of he barcodes can be tailored as needed. As will be noted below, 262,144 error-correctable barcodes can used in a single-end sequencing context to discriminate between the amplification products of 262,144 different starting molecules, even if the starting molecules have the same sequence. If paired end sequencing is used (in which case the barcode on both ends of the molecules are sequenced), the barcodes can discriminate between 262,$144^2$ (i.e., over 69 billion) different starting molecules, even if the starting molecules have the same sequence.

As described in the Examples section herein, the nucleic acid adaptors may further comprise a random sequence of 4 to 8 nucleotides between regions X and Y for some applications. Further, one or both strands of the adaptors may comprises one or more nuclease-resistant linkages (particularly at the 3' ends of the strands), thereby protecting the adaptors from degradation by a nuclease.

The concentration of the adaptors in the composition may vary. In some embodiments, the adaptors may be in dry form or in an aqueous solution, e.g., at a concentration of at least 100 nM, e.g., at least 500 nm, at least 1 µM, at least 2 µM or at least 5 µM. There may be at least 100,000, e.g., at least 1M molecules of the each sequence in the composition.

In some embodiments, region X may be 12-50 nt in length, region Y may be 20-50 nucleotides in length and region Z may be 10-50 nucleotides in length.

The adaptor composition described above may be used in a variety of methods. For example, in some embodiments, the composition may be used to tag a sample of double-stranded DNA. In some embodiments, this method may be done with the "Y" adaptor configuration of the adaptor and, as such, the method may comprise obtaining (e.g., receiving) a subject population of nucleic acid adaptors, where region X comprises top and bottom strands that are not complementary. This method may comprise attaching the nucleic acid adaptors to the fragments of the double-stranded DNA (double-stranded cDNA or genomic DNA), by ligation or using a transposase, thereby tagging the double-stranded DNA with the different molecular barcode sequences. As would be apparent, if the tagging is catalyzed by a transposase, then the adaptors should contain a transposon end sequence. In these embodiments, the adaptors are loaded onto the transposase (two per transposase) and used to tagment the double stranded DNA using a method adapted from, e.g., Picelli et al, Genome Res. 2014 24: 2033-40; Adey et al, Genome Biol. 2010 11:R119 and Caruccio et al, Methods Mol. Biol. 2011 733: 241-55, US20100120098 or US20130203605. If the tagging is catalyzed by a ligase (e.g., T4 DNA ligase or the like), then the adaptors should contain a ligatable end, e.g., a blunt end or a 3' or 5' overhang such as a 5' T overhang, and the adaptors are ligated onto fragmented DNA (e.g., DNA that has been fragments using physical methods (e.g., sonication, nebulization, or shearing), chemically or enzymatically (e.g., using restriction enzyme or the like) and optionally end-polished. In some embodiments, prior to sequencing, the tagged DNA may be amplified using first primer that has the same sequence as at least part of the top strand of region X and a second primer that is complementary to the bottom strand of X.

Figure 3:
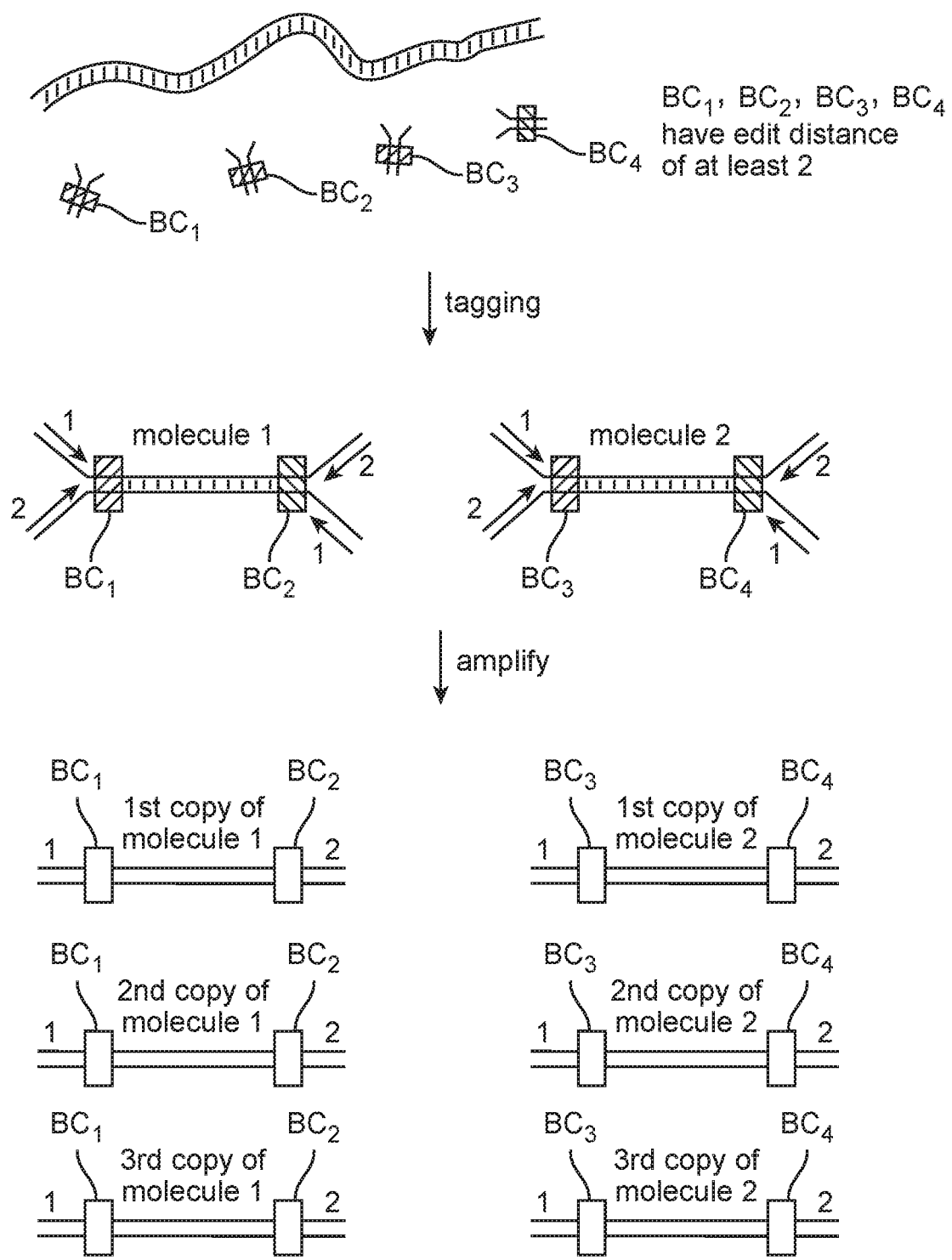
FIG. 3 schematically illustrates one way in which the present adaptors can be used to tag a sample.

Some principles of this method are schematically illustrated in FIG. 3. As illustrated, double-stranded DNA is tagged (e.g., tagmented) with Y-adaptors containing barcodes 1, 2, 3, and 4 ($BC_1$, $BC_2$, $BC_3$ and $BC_4$), to produce tagged molecule 1 and tagged molecule 2. These molecules could, in theory, have the same sequence (including the same junctions with the adaptors) and, as such, the sequence reads for those molecules will be indistinguishable. As shown, tagged molecule 1 and tagged molecule 2 are amplified using primers 1 and 2 (where primer 1 has the same sequence as the top strand of region X and primer 2 is complementary to the bottom strand of region X) to produce multiple copies of molecule 1 and multiple copies of molecule 2, where all of the copies of molecule 1 are tagged by $BC_1$ and $BC_2$, and all of the copies of molecule 2 are tagged by $BC_3$ and $BC_4$. After sequencing, the starting molecules can be readily distinguished by the barcodes in the sequence reads.

In another embodiment, the bottom strand of the population of adaptors may be removed, e.g., by degrading the bottom strand of the nucleic acid adaptors of (a) using an exonuclease or by removing the bottom strand of the nucleic acid adaptors by affinity (e.g., using a biotin tag added to the bottom strand) to produce set of barcoded primers. In these embodiments, the method may comprise (a) obtaining a population of nucleic acid adaptors of claim 1, wherein region Z is a primer sequence comprising a 3' hydroxyl and the top strand of Z may end in a random sequence, a sequence-specific primer, or an oligo-dT. This method may comprise (b) isolating the top strand of the nucleic acid adaptors from the bottom strand of the nucleic acid adaptors, thereby producing a population of primers of formula X-Y-Z, wherein region X comprises an amplification sequence, region Y comprises a molecular barcode having a variable sequence, and region Z comprises the primer sequence comprising a 3' hydroxyl; wherein: (i) there are at least 50,000 different molecular barcode sequences in the set; and (ii) at least 90% of the molecular barcode sequences have an edit distance of at least 2. In some embodiments, this method may comprise copying a template (e.g., mRNA, cDNA or genomic DNA) in a sequence-specific or non-sequence specific (e.g., using a primer that has a random sequence or oligo-dT at the end) way using the barcoded primers, thereby tagging the complement of the template with at least 50,000 different molecular barcode sequences, wherein at least 90% of the molecular barcode sequences have an edit distance of at least 2; and amplifying the product of b) using a reverse primer and primer that has the same sequence as at least part of the amplification sequence of X and a second primer.

Figure 4:
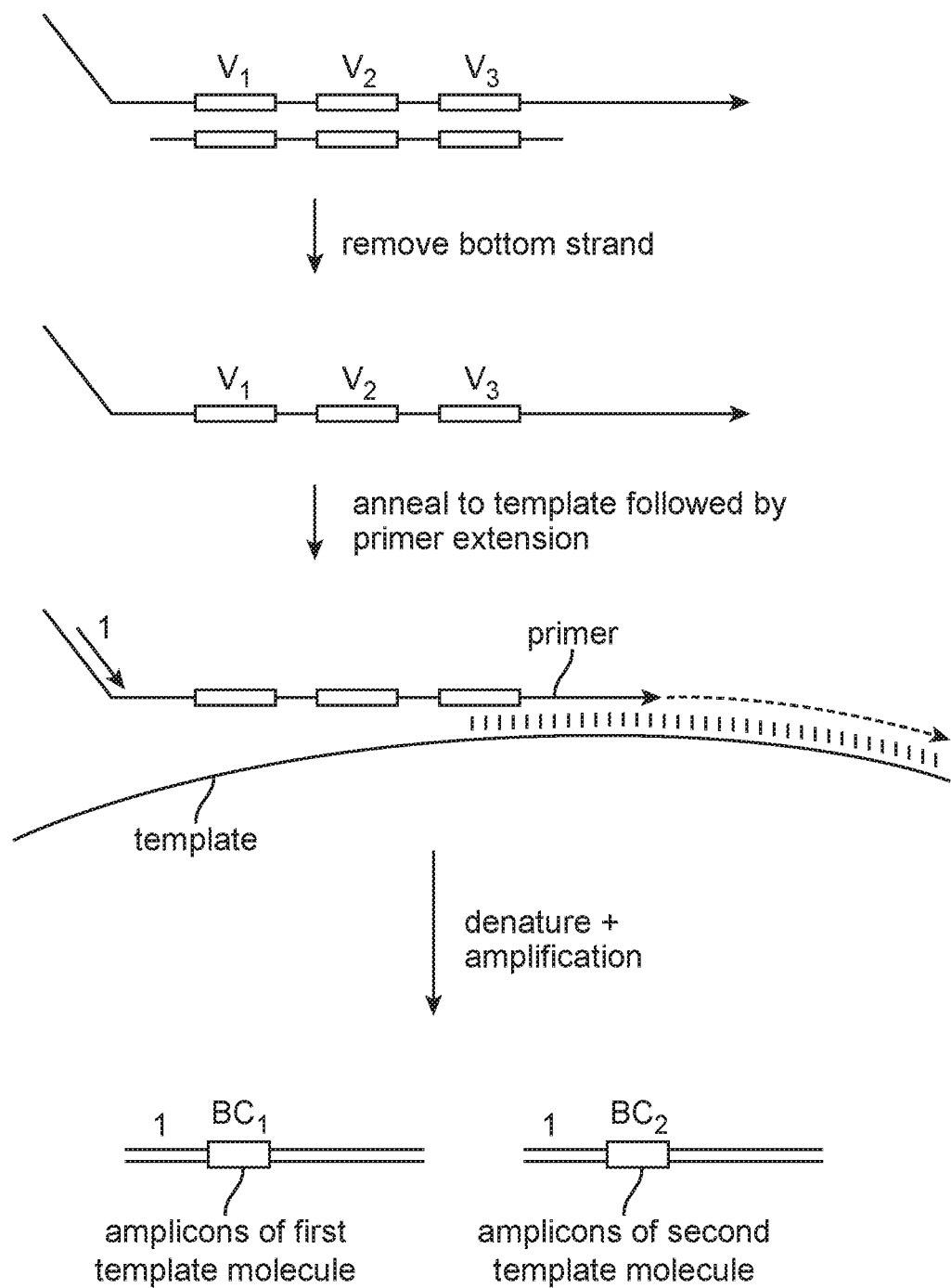
FIG. 4 schematically illustrates how the present adaptors can be converted into primers and used to tag a sample by primer extension.

Some principles of this embodiment of the method are schematically illustrated in FIG. 4. As shown in FIG. 4, the bottom strand of the adaptors may be removed using an exonuclease (e.g., T4 exonuclease) to produce a set of primers that have 50,000 different molecular barcode sequences, at least 90% of which have an edit distance of at least 2. These primers may be annealed to a template (e.g., RNA, genomic DNA or cDNA or the like) and extended. After removal of excess primers, the primer extension product may be amplified using primer 1 and another primer that is complementary to a site that is downstream in the product (which may have been added onto the product or may already be in the product). This amplification reaction will produce amplicons of different template molecules, where each amplicon is tagged with a different barcode (e.g., $BC_1$ and $BC_2$, as shown). The different template molecules can therefore be distinguished by their barcodes.

Figure 6A:
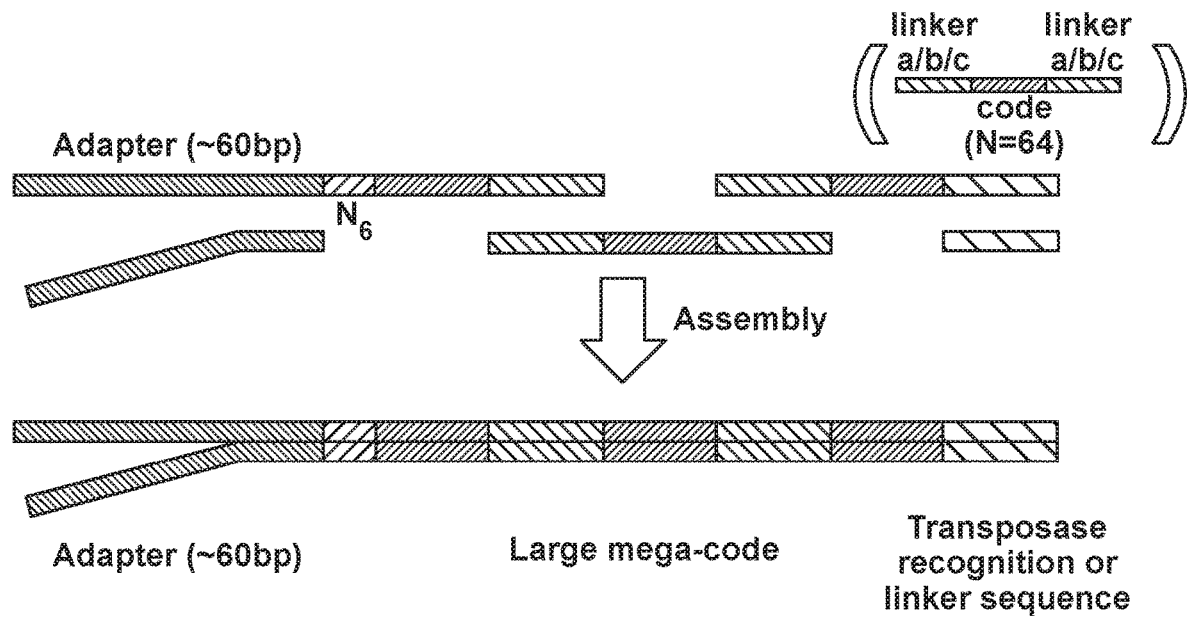
FIGS. 6A-6D illustrate one implementation of the method as well as exemplary results from the same.
Figure 6A:
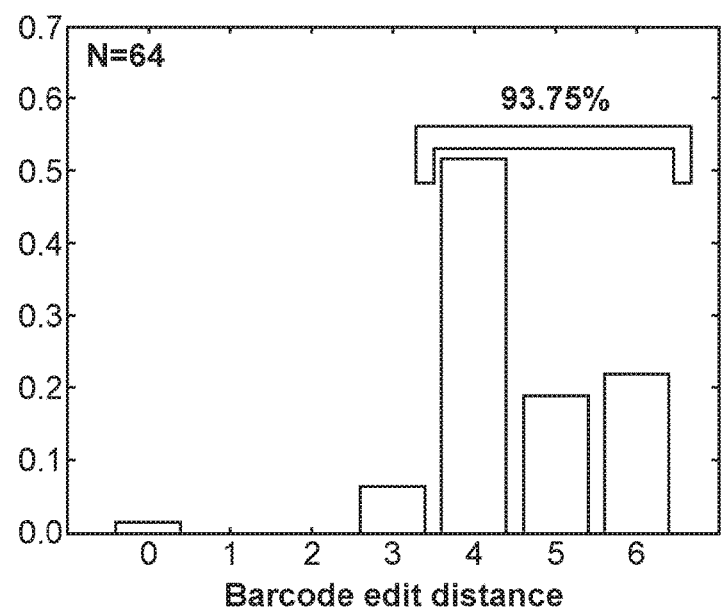

As noted above and as will be described in greater detail below, as complex is the present population of adaptors is, it can be made with relatively few oligonucleotides, e.g., less than 100, less than 200, or less than 500 oligonucleotides of a defined (i.e., not random) sequence. In the example reduced to practice in the experimental section of the present application (see FIG. 6A, a total of 194 oligonucleotides were used. Of the 194 oligonucleotides, two oligonucleotides had a non-varying sequence that becomes the 5' and 3' ends of the bottom strand of the adaptors and the remaining 192 adaptors are composed of three sets of 64 adaptors that each contributes sequences to a different module of a three module discontinuous barcode. Each oligonucleotide in the first set of 64 oligonucleotides has (i) the same 5' arm (which becomes one of the arms of a Y adaptor), (ii) a central defined, non-random, 6 base sequence that is becomes the first module of the barcode, and (iii) a 3' arm that hybridizes to a complementary arm in the third set of oligonucleotides. Each oligonucleotide in the second set of 64 oligonucleotides has (i) a 5' arm that hybridizes to a complementary sequence in the third set of oligonucleotides, (ii) a central defined, non-random, 6 base sequence that is becomes the third module of the barcode, and (iii) a defined sequence that could be the top strand of a transposase sequence or a linker sequence. Each molecule in the third set of 64 oligonucleotides has (i) a 5' arm that hybridizes to a complementary sequence in the second set of oligonucleotides, (ii) a central defined, non-random, 6 base sequence that is becomes the second module of the barcode, and (iii) a 3' arm that hybridizes to a complementary sequence in the first set of oligonucleotides. As shown in FIG. 6A, the various oligonucleotides and be annealed to one another in a single tube and joined to one another in an extension ligation reaction (where the barcode sequences are copied by the polymerase, thereby making that least that section of the adaptor double-stranded).

Figure 5:
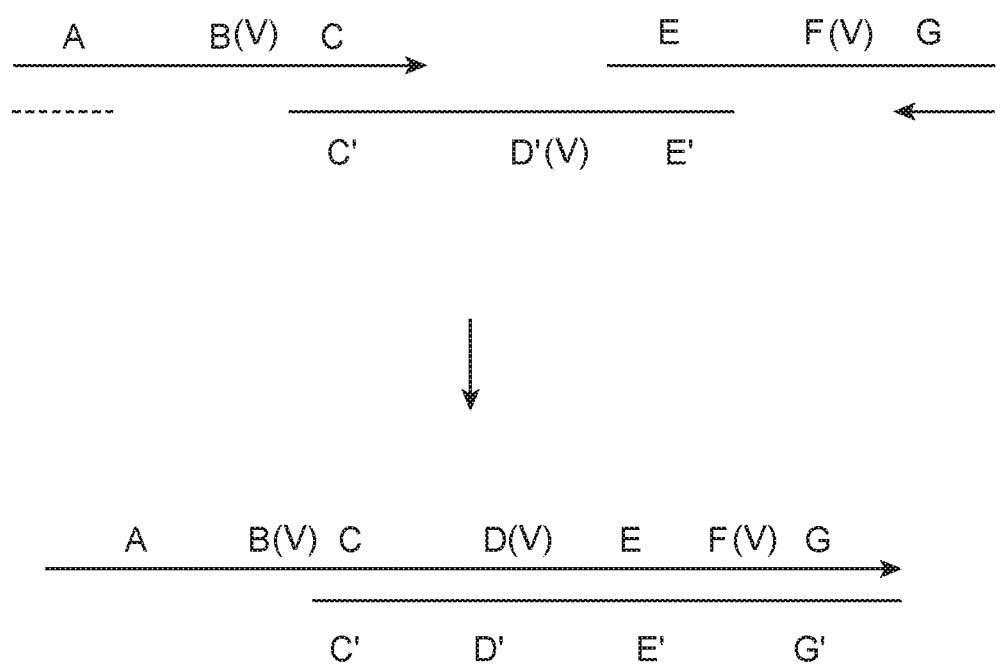
FIG. 5 schematically illustrates a way to make the present adaptor population.

In certain embodiments and as shown in FIG. 5, this method may comprise: (a) annealing together: a first population of oligonucleotide of formula A-B-C, a second population of oligonucleotide of E-F-G, a third population of oligonucleotides of formula C'-D'-E' and a fourth oligonucleotide of sequence G', wherein: (i) the sequences of B, D' and F vary from molecule to molecule but are not random or semi-random; (ii) sequences B, the complements of D' and F, are combinable to produce at least at least 50,000 different molecular barcode sequences; (iii) at least 90% of the molecular barcode sequences sequence produced by combining sequence B, the complement of sequence D' and sequence G are have an edit distance of at least 2; (iv) sequences C and C' are at least partially complementary, sequences E and E' are at least partially complementary and sequences G and G' are at least partially complementary; and (v) sequence G comprises a 3' hydroxyl or is the top strand of a transposon end sequence. After the annealing is done, the method may comprise (b) extending the first population of oligonucleotides by primer extension using a non-strand displacing polymerase; and (c) joining the extension products of (b) to the third population of oligonucleotides, thereby producing a population of nucleic acid adaptors that comprises at least 50,000 different molecular barcode sequences in which at least 90% of the molecular barcode sequences have an edit distance of at least 2. As would be appreciated steps (b) and (c) may be done in the same reaction.

In any embodiment, the tagged fragments may be sequenced directly or, in some embodiments, the released fragments may be amplified (e.g., by PCR) to produce amplification products that sequenced. In certain embodiments, amplification products may contain sequences that are compatible with use in, e.g., Illumina's reversible terminator method, Roche's pyrosequencing method (454), Life Technologies' sequencing by ligation (the SOLiD platform) or Life Technologies' Ion Torrent platform, as described above. In other words, tagging the tagged DNA may be optionally amplified (e.g., using primers that hybridize to the added adaptor sequences or their complements) and sequenced. In certain embodiments, the released DNA may be amplified using primers that are compatible with use in, e.g., Illumina's reversible terminator method, Roche's pyrosequencing method (454), Life Technologies' sequencing by ligation (the SOLiD platform) or Life Technologies' Ion Torrent platform. Examples of such methods are described in the following references: Margulies et al (Nature 2005 437: 376-80); Ronaghi et al (Analytical Biochemistry 1996 242: 84-9); Shendure et al (Science 2005 309: 1728-32); Imelfort et al (Brief Bioinform. 2009 10:609-18); Fox et al (Methods Mol Biol. 2009; 553:79-108); Appleby et al (Methods Mol Biol. 2009; 513:19-39) and Morozova et al (Genomics. 2008 92:255-64), which are incorporated by reference for the general descriptions of the methods and the particular steps of the methods, including all starting products, reagents, and final products for each of the steps.

In another embodiment, the tagged DNA may be sequenced using nanopore sequencing (e.g., as described in Soni et al. Clin. Chem. 2007 53: 1996-2001, or as described by Oxford Nanopore Technologies). Nanopore sequencing is a single-molecule sequencing technology whereby a single molecule of DNA is sequenced directly as it passes through a nanopore. A nanopore is a small hole, of the order of 1 nanometer in diameter. Immersion of a nanopore in a conducting fluid and application of a potential (voltage) across it results in a slight electrical current due to conduction of ions through the nanopore. The amount of current which flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore represents a reading of the DNA sequence. Nanopore sequencing technology is disclosed in U.S. Pat. Nos. 5,795,782, 6,015,714, 6,627,067, 7,238,485 and 7,258,838 and U.S. Pat Appln Nos. 2006003171 and 20090029477.

The barcode sequence may be identified in the sequence reads, and used to identify sequence errors, for allele calling, for assigning confidence, to perform copy number analysis and to estimate gene expression levels using methods that can be adapted from known methods, see, e.g., Casbon (Nucl. Acids Res. 2011 39: e81), Fu (Proc. Natl. Acad. Sci. 2011 108: 9026-9031) and Kivioia (Nat. Methods 2011 9: 72-74). The error correctable barcodes make such analyses more accurate because, even if one barcode is mis-read, the error can be corrected or the read can be eliminated.

In certain embodiments, the sample sequenced may comprise a pool of nucleic acids from a plurality of samples, wherein the nucleic acids in the sample have a different molecular barcode to indicate their source. In some embodiments the nucleic acids being analyzed may be derived from a single source (e.g., from different sites or a timecourse in a single subject), whereas in other embodiments, the nucleic acid sample may be a pool of nucleic acids extracted from a plurality of different sources (e.g., a pool of nucleic acids from different subjects), where by "plurality" is meant two or more. As such, in certain embodiments, a nucleic acid sample can contain nucleic acids from 2 or more sources, 3 or more sources, 5 or more sources, 10 or more sources, 50 or more sources, 100 or more sources, 500 or more sources, 1000 or more sources, 5000 or more sources, up to and including about 10,000 or more sources. These molecular barcodes allow the sequences from different sources to be distinguished after they are analyzed. Such barcodes may be added during the amplification process (after tagging with the barcodes contained within the adaptors).

A population of double stranded DNA fragments, wherein the DNA fragments are tagged with at least 50,000 different molecular barcode sequences, wherein at least 90%, e.g., at least 95%, of the molecular barcode sequences have an edit distance of at least 2, e.g., at least 3, at least 4 or at least 5. In some embodiments, the double stranded DNA fragments are genomic DNA. In other embodiments, the double stranded DNA fragments are cDNA. The fragments may have a median size in the range of 100 bp to 10 kb (e.g., 200 bp to 2 kb) and in some cases at least 99% of the fragments each may be asymmetrically tagged in that the top strand of the fragments has one barcode sequence at the 5' end and another barcode sequence at the 3' end.

Kits

Also provided by the present disclosure are kits for practicing the subject method as described above. In certain embodiments, a subject kit may contain a population of adaptors described above. The kit may also contains other reagents described above and below that may be employed in the method, e.g., a transposase, ligase or polymerase, etc., depending on how the adaptors are going to be employed.

In addition to above-mentioned components, the subject kit typically further includes instructions for using the components of the kit to practice the subject method. The instructions for practicing the subject method are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

In order to further illustrate the present invention, the following specific examples are given with the understanding that they are being offered to illustrate the present invention and should not be construed in any way as limiting its scope.

EXAMPLES

Aspects of the present teachings can be further understood in light of the following example, which should not be construed as limiting the scope of the present teachings in any way.

Demonstrated herein is a strategy to introduce a unique variant of DNA barcodes that can robustly identify the single-molecule origin of a next-generation sequencing read from sequencing libraries and scale from billions to over trillions of unique species without prior knowledge of the DNA insert context. It is based on the combinatorial assembly of a small set of rationally designed error-resistant oligonucleotides that allow for an exponential expansion in the total number of possible barcodes comparable to methods utilizing random nucleotides.

In this study, results from coding theory were used to construct a small number of barcodes that maximized the edit distance between them (FIG. 6A). Using an optimal Hamming generator matrix for a symbol size of four, we are able to efficiently generate barcodes with algorithmically constant time scaling. Alternative techniques of rational barcode generation through simulation is computationally intensive and requires exponential amounts of time with increasing barcode diversity. A total of 192 variable and 2 constant oligonucleotides were synthesized that, when assembled using an optimized extension ligation reaction, resulted in over 69 theoretically billion uniquely identifiable paired-end barcodes, and $64^3=262,144$ barcodes in a single-ended sequencing context. In addition, with our method longer barcode subunits are possible through the simple computation of larger optimized Hamming matrices. Other error-coding strategies have been utilized but, to our best knowledge, optimized half-rate barcodes as demonstrated in this work are the most efficient for DNA-based systems with moderate symbol size. Such rationally designed barcodes can be combined in a variety of assembly reaction formats, and introduced into DNA inserts via a ligation or transposase-based process.

Figure 6B:
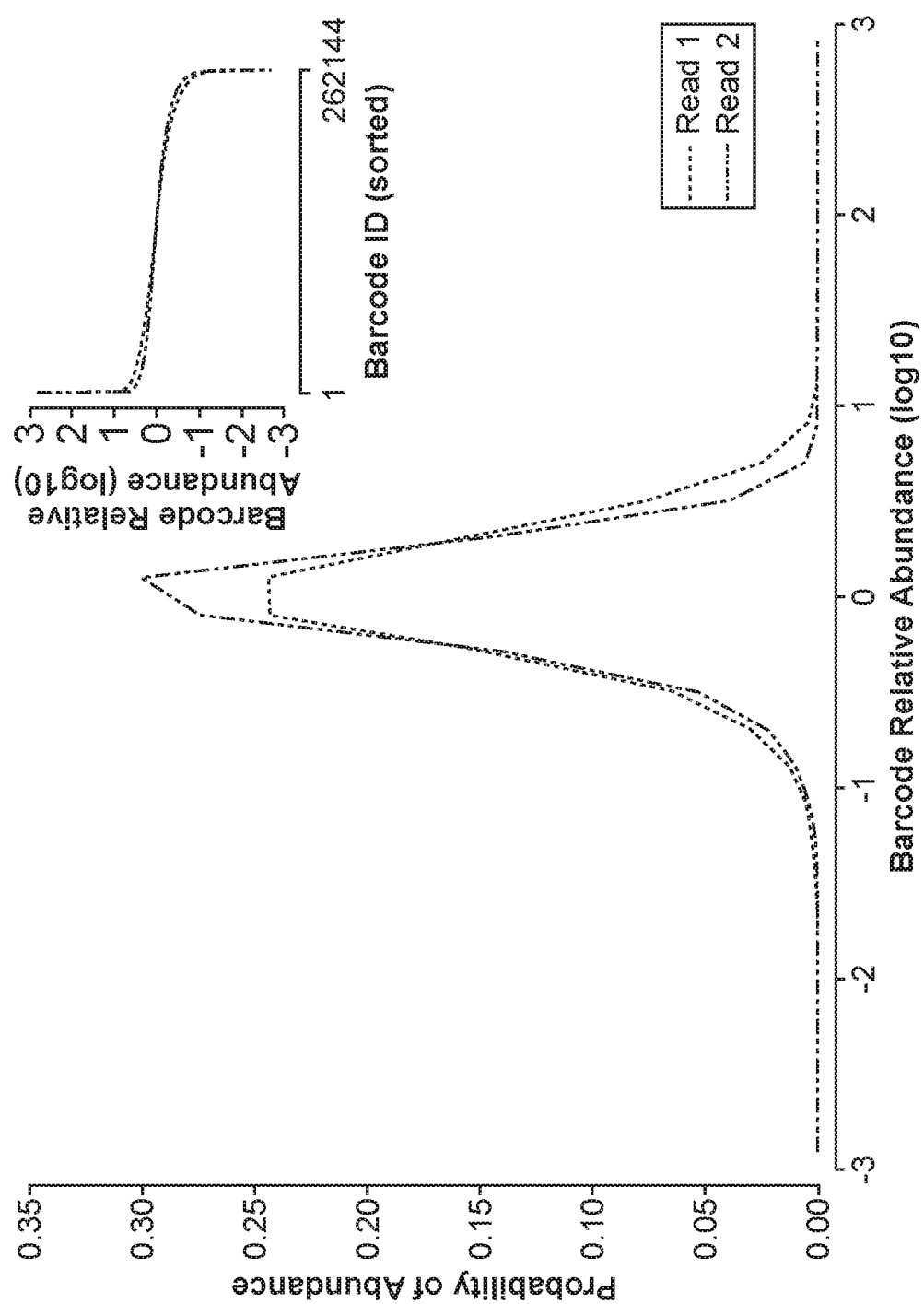
Figure 6C:
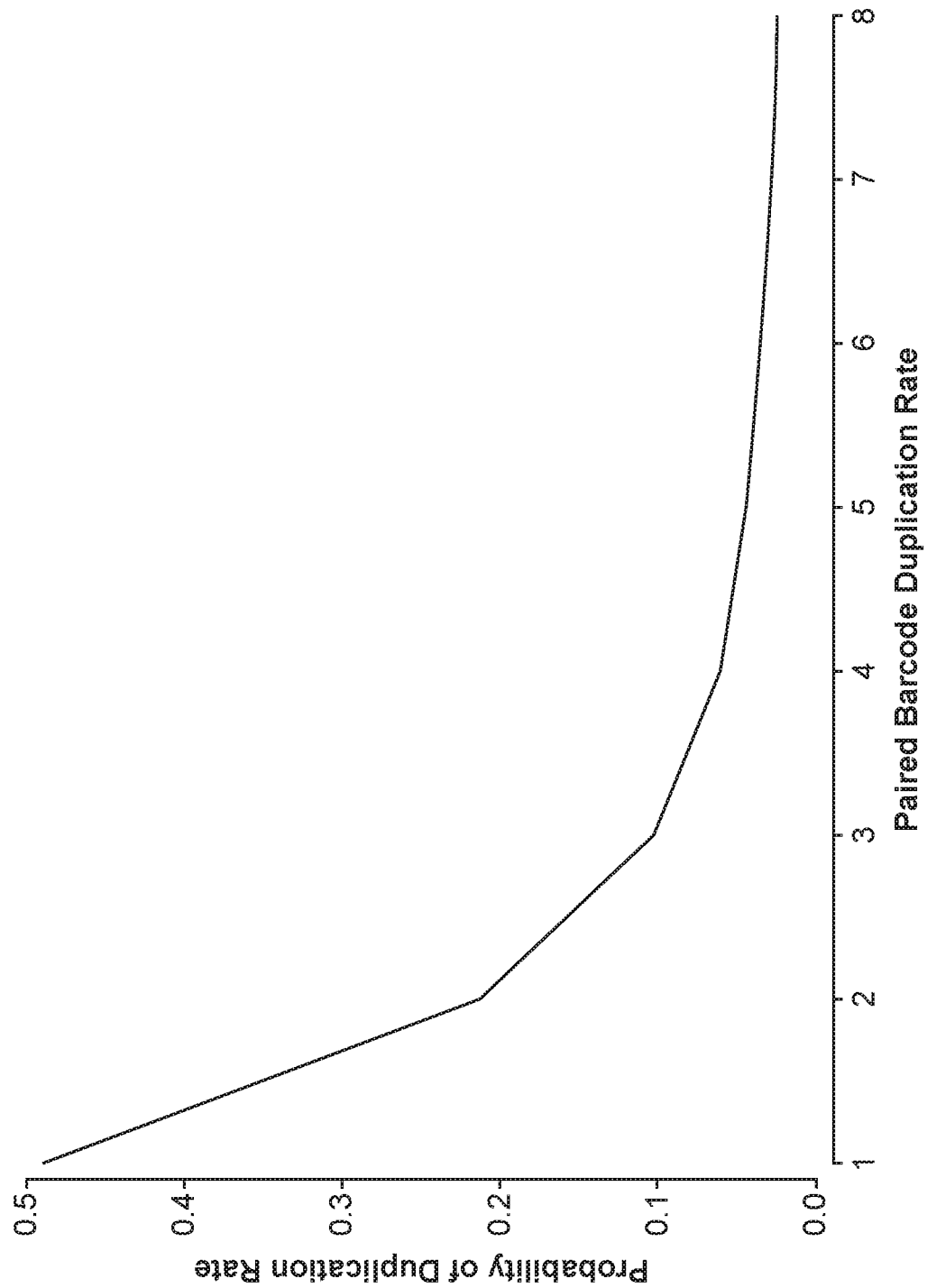
Figure 6D:
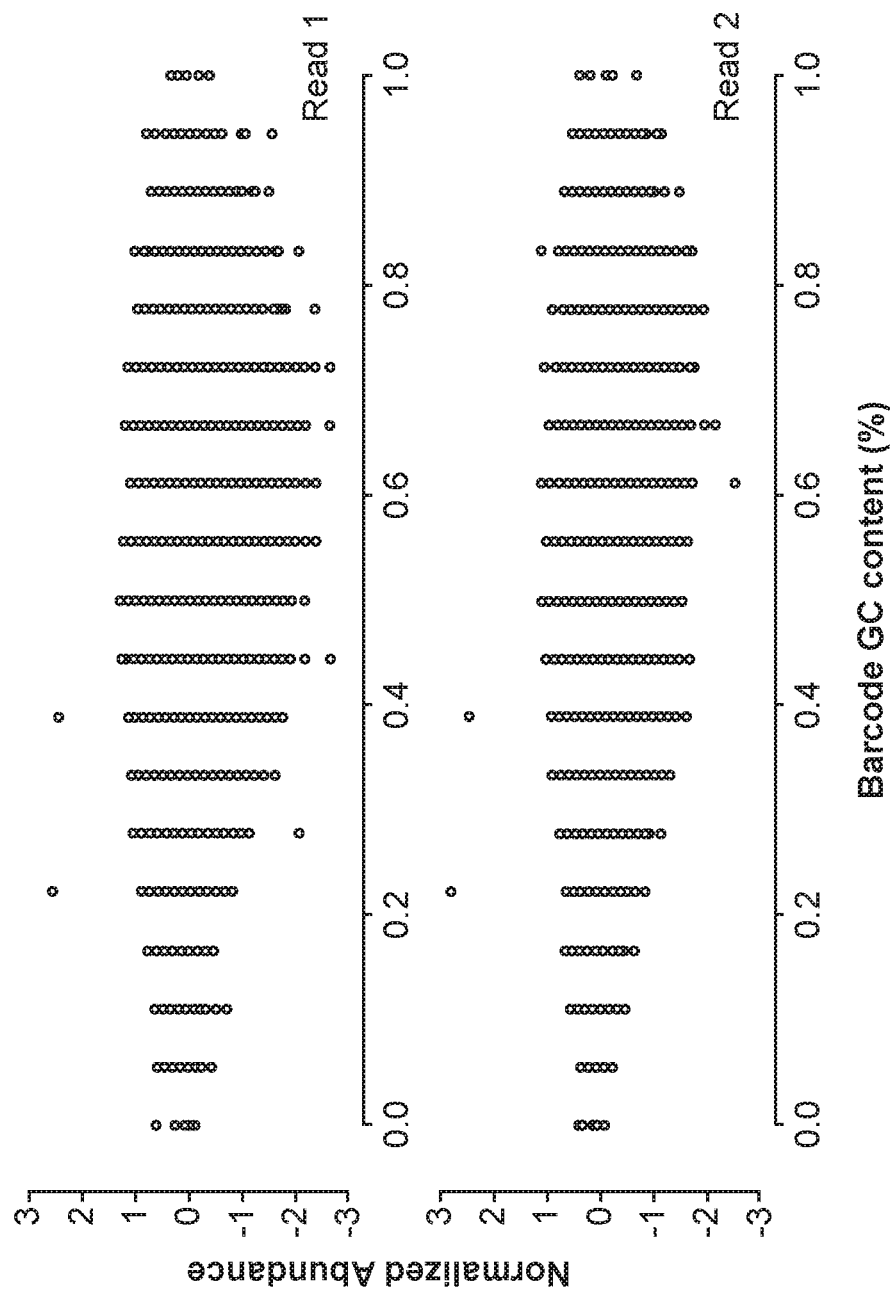

To assess the barcode performance, these barcodes were introduced to 50 ng of randomly sheared genomic DNA library of a Yoruban (NA18507) individual and recovered 100% of all possible single-end barcodes from only the first or second read. The extent of possible bias in barcode incorporation was investigated; by using only barcode abundances from unpaired reads we determine that over 98% of these sequences have abundances within a logarithm of the median abundance (FIG. 6B). Little correlation between GC content and barcode abundance (FIG. 6D) was observed.

Quantification errors may be prevalent in RNA-Seq studies due to the significantly smaller size of human transcriptomes compared to that of the human genome. The performance of molecular barcoding in measuring transcript abundances as compared to standard shotgun RNA-Seq methods was assessed. Stranded RNA-Seq libraries were prepared using a modified transposase approach and incorporated in triplicate these molecular barcodes into human RNA standards used for the MAQC and SEQC studies. When extracting only the molecular barcodes independent of the context of the insert sequence, a median molecular duplication rate of 1 was observed but significant fractions of reads that appear to be duplicated as a long-tailed distribution. Pearson coefficients of less than 0.1 across all samples when performing a simple correlation analysis of paired-end barcode abundances were observed, indicating a lack of systematic bias in amplification due to either the insert or barcode sequence. As a comparison to molecular barcoding by random sequences, the first random 6 bp of each sequencing read was used to form a paired 12 bp random barcode with a total diversity of ~16.7 million. For each sequencing read identified as belonging to a unique molecule, a sequencing error occurred in 2.4% of duplicated barcodes across all tested RNA-Seq libraries was determined. Without an inline barcode control as demonstrated in this work, the extensive error found in random barcodes prevents accurate quantification as it would be otherwise impossible to detect whether an error occurred.

Figure 7A:
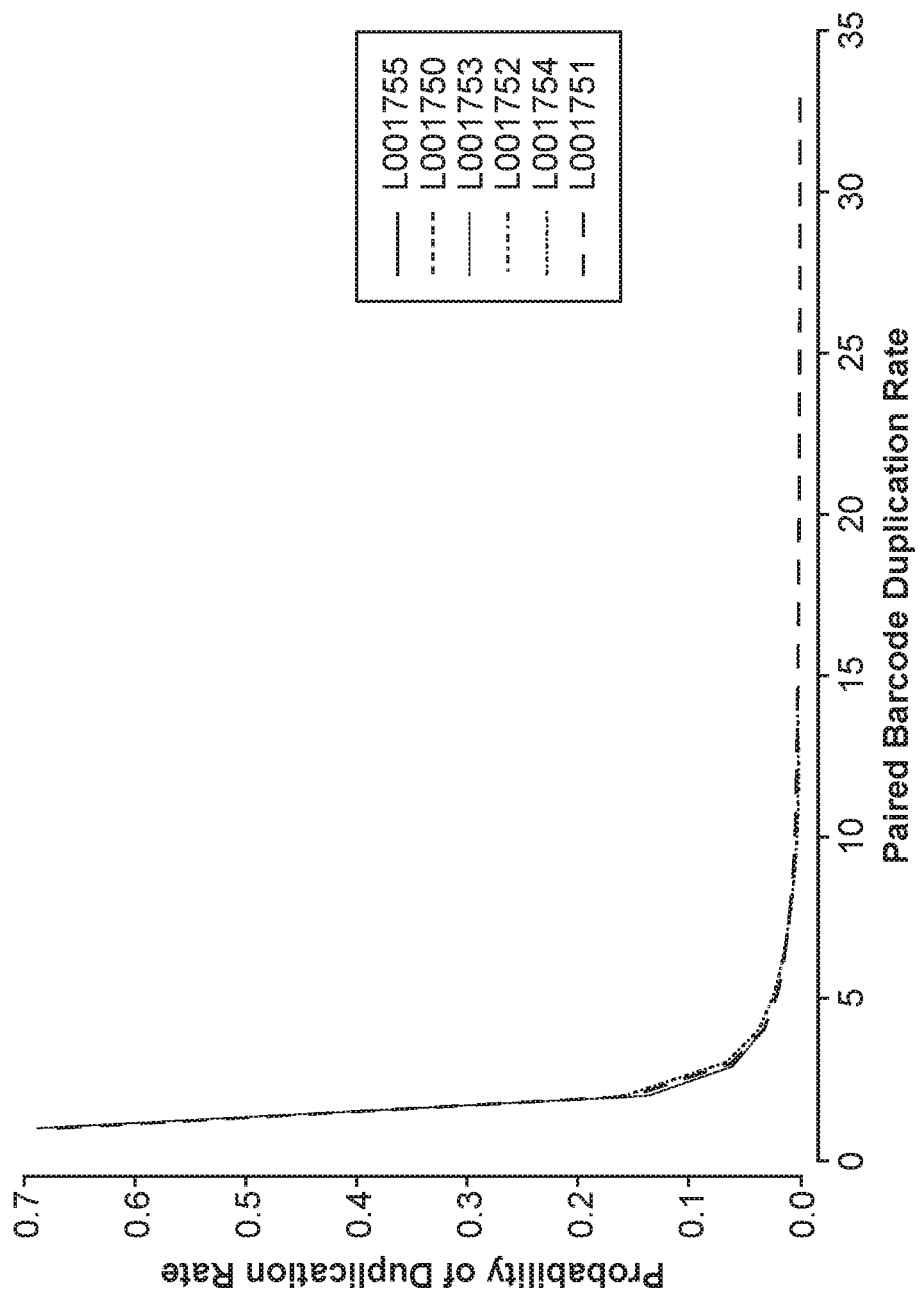
FIGS. 7A-7E show results obtained from the present method.
Figure 7B:
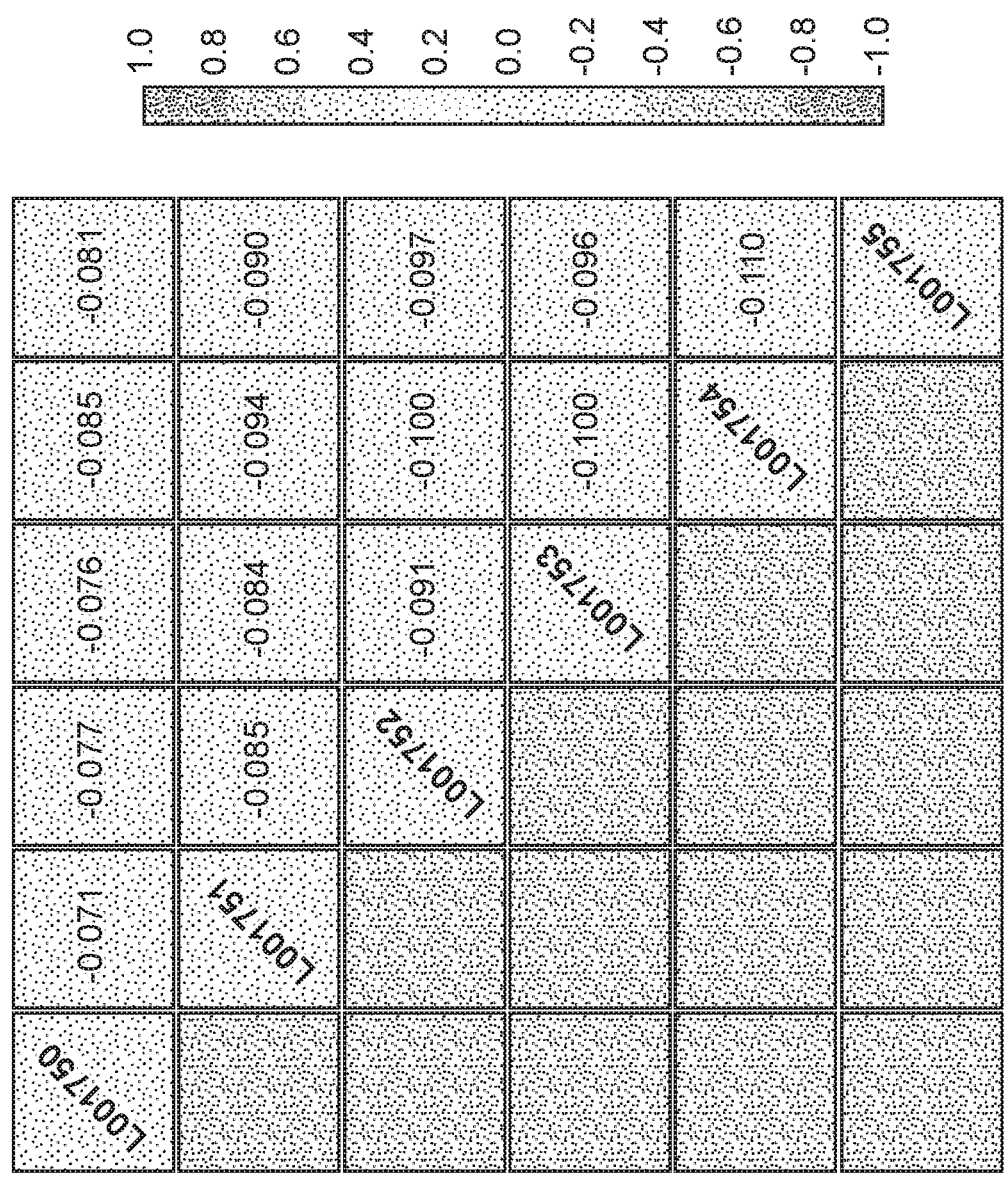
Figure 7C:
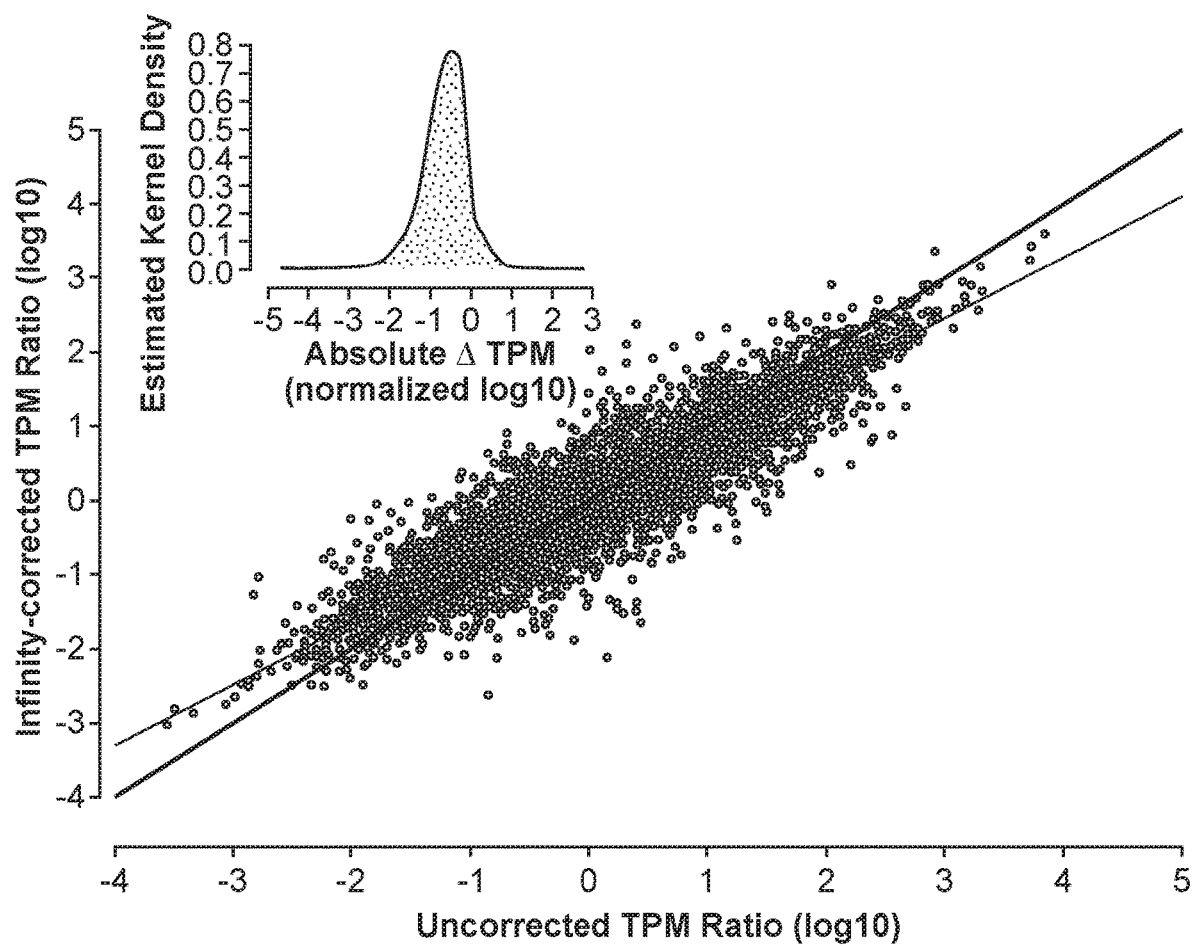
Figure 7D:
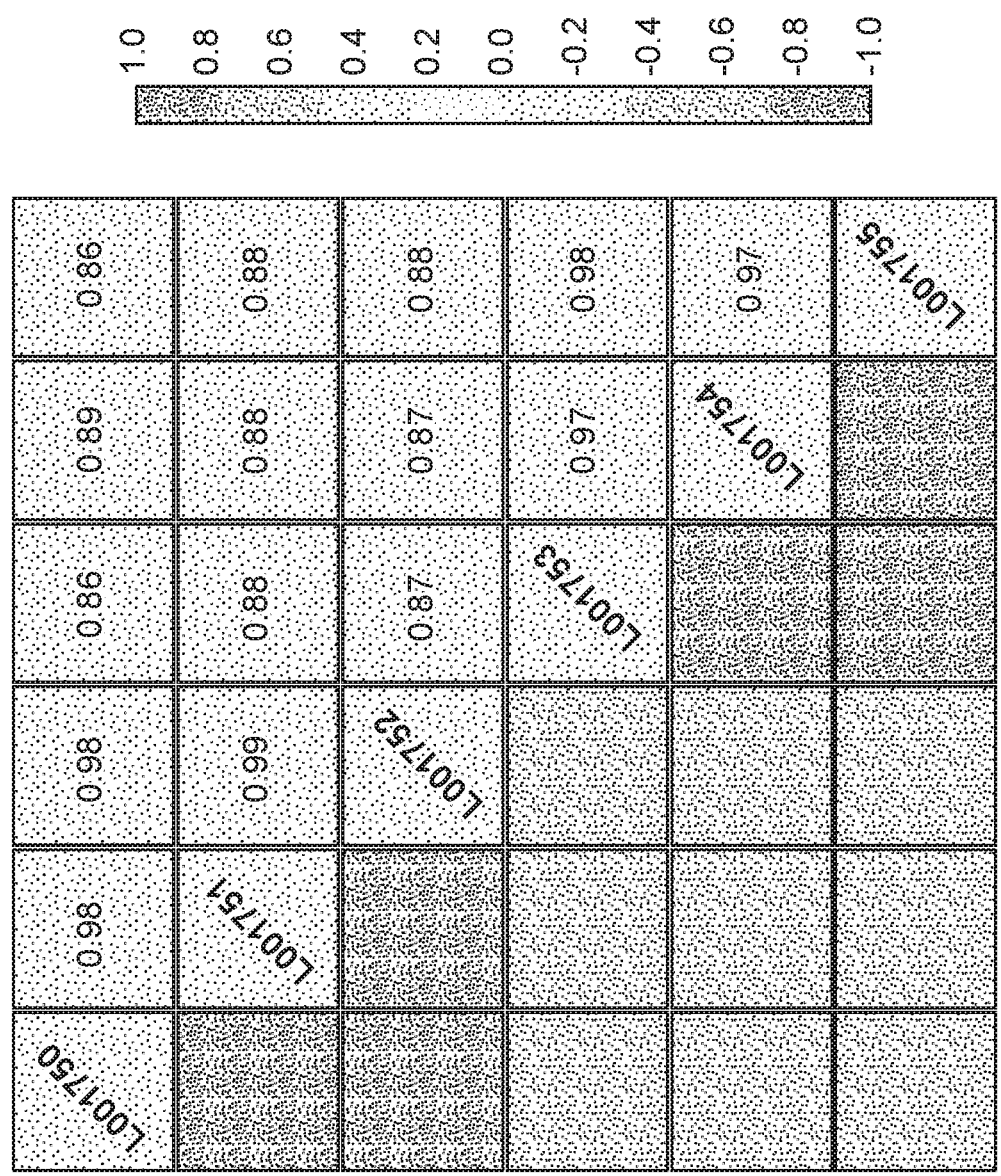
Figure 7E:
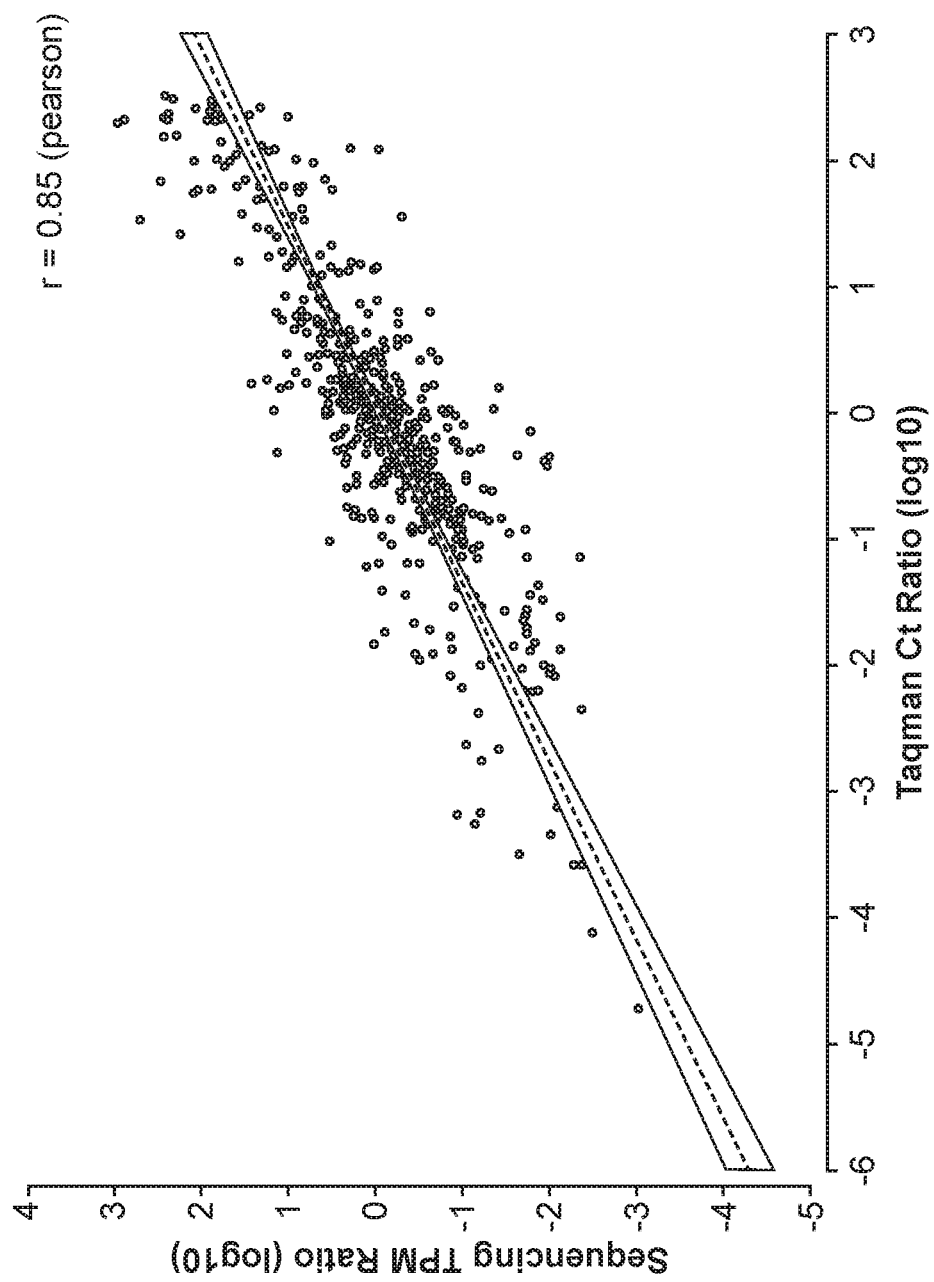

The fold-change in gene expression (transcripts per million; TPM) was assessed between the average gene expression of two standards (eg. Brain versus UHRR RNA standards) as corrected by molecular barcoding versus the uncorrected control. While in general the quantification values are, in logarithmic scale, linearly correlated across the transcriptome, the majority of genes have a corrected abundance that is lower by approximately an order of magnitude (FIG. 7C). In order to determine the degree by which the two RNA standards differed, a correlation analysis of transcript abundances between the two sample types was observed and indeed the technical replicates indeed clustered together with a within-sample Pearson correlation coefficient of over 0.98 across all genes, versus a Pearson correlation coefficient of 0.85-0.89 between technical replicates across different sample types (FIG. 2D). To account for anomalous errors in gene expression quantification, RNA-Seq data as corrected by molecular barcodes versus existing RT-qPCR data were compared for approximately 1000 genes. Here a correlation coefficient of ~0.85 when comparing fold-changes in gene expression (FIG. 7E) was observed, which is comparable to typical correlations between RNA-Seq and RT-qPCR data. Therefore, shotgun RNA-Seq studies may systematically overestimate transcript abundances due to the uncorrected duplication of molecular species as found in high-depth sequencing.

What is claimed is:
1. A method for making a population of nucleic acid adaptors, comprising:
   (a) annealing together:
      (i) a first population of synthetic oligonucleotides of formula-A-B-C,
      (ii) a second population of synthetic oligonucleotides of formula E-F-G,
      (iii) a third population of synthetic oligonucleotides of formula C'-D'-E' and
      (iv) a fourth oligonucleotide of sequence G',
   wherein A, B, and C are subsequences of the synthetic oligonucleotides of the first population; E, F, and G are subsequences of the synthetic oligonucleotides of the second population, and C', D', and E' are subsequences of the synthetic oligonucleotides of the third population, and each of the synthetic oligonucleotides of the first population, the second population and the third population is in the range of 20-150 nucleotides in length,
   to produce complexes in which subsequence C is annealed to subsequence C', subsequence E is annealed to subsequence E', subsequence G is annealed to sequence G' and subsequences D' and F are single-stranded;
      wherein subsequences B, D' and F vary and are defined sequences in the first, second, and the third populations of the synthetic oligonucleotides and subsequences A, C, E, G, C' and E' do not vary in the first, second, and the third populations of the synthetic oligonucleotides; and
      subsequence G comprises a 3' hydroxyl or a transposon end sequence;
   (b) adding subsequences D and F' to the complexes by extending the first population of synthetic oligonucleotides and the fourth oligonucleotide in the complexes by primer extension using a non-strand displacing polymerase; and
   (c) ligating the complexes to produce a population of nucleic acid adaptors, wherein;
      (i) the population of nucleic acid adaptors does not comprise any genomic DNA; and
      (ii) the complexes comprise at least 50,000 different molecular barcode sequences composed of subsequences B, D and F.
2. The method of claim 1, wherein the at least 50,000 different molecular barcode sequences of (c)(ii) have a length of at least 13 nucleotides.

3. The method of claim 1, wherein subsequence B, subsequence D and subsequence F are each 5-7 nucleotides in length.

4. The method of claim 1, wherein at least one of the synthetic oligonucleotides comprises one or more nuclease-resistant linkages, thereby protecting the population of nucleic acid adaptors of (c) from degradation by a nuclease.

5. The method of claim 1, wherein subsequence G is a transposon end sequence.

6. The method of claim 1, wherein subsequence G comprises a 3' hydroxyl, thereby allowing the population of nucleic acid adaptors of (c) to be ligated to double stranded DNA.

7. The method of claim 1, further comprising:
 (d) attaching the nucleic acid adaptors from the population of nucleic acid adaptors produced in step (c) to fragments of the double-stranded DNA, by ligation or using a transposase, thereby producing a population of tagged nucleic acid adaptors comprising different fragments of the double-stranded DNA tagged with different molecular barcode sequences from at least 50,000 different molecular barcode sequences.

8. The method of claim 7, wherein the fragments are double-stranded cDNA or genomic DNA.

9. The method of claim 1, wherein the population of nucleic acid adaptors produced ire step (c) are in an aqueous solution at a concentration of at least 1 micromolar (µM).

\* \* \* \* \*